US007449297B2

(12) United States Patent
Freije et al.

(10) Patent No.: US 7,449,297 B2
(45) Date of Patent: Nov. 11, 2008

(54) METHODS OF COPYING THE METHYLATION PATTERN OF DNA DURING ISOTHERMAL AMPLIFICATION AND MICROARRAYS

(75) Inventors: Wadiha Freije, Forest Park, IL (US); Igor Brikun, Forest Park, IL (US)

(73) Assignee: Euclid Diagnostics LLC, Crown Point, IN (US)

( * ) Notice: Subject to any disclaimer, the term of this patent is extended or adjusted under 35 U.S.C. 154(b) by 0 days.

(21) Appl. No.: 11/402,681

(22) Filed: Apr. 11, 2006

(65) Prior Publication Data
US 2006/0257905 A1 Nov. 16, 2006

Related U.S. Application Data

(60) Provisional application No. 60/671,193, filed on Apr. 14, 2005.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................... 435/6; 536/23.1; 435/91.2
(58) Field of Classification Search .................. None
See application file for complete search history.

(56) References Cited

U.S. PATENT DOCUMENTS

| 5,043,272 A | 8/1991 | Hartley |
| 5,939,258 A | 8/1999 | Croce et al. |
| 6,124,120 A | 9/2000 | Lizardi |
| 6,143,495 A | 11/2000 | Lizardi et al. |
| 6,280,949 B1 | 8/2001 | Lizardi |
| 6,287,820 B1 | 9/2001 | Umansky et al. |
| 6,514,698 B1 | 2/2003 | Lopez et al. |
| 6,610,488 B2 | 8/2003 | Danenberg et al. |
| 6,613,518 B2 | 9/2003 | Danenberg et al. |
| 6,617,137 B2 * | 9/2003 | Dean et al. .................. 435/91.1 |
| 6,783,943 B2 | 8/2004 | Christian et al. |
| 2004/0063144 A1 | 4/2004 | Lizardi |
| 2004/0126764 A1 | 7/2004 | Lasken et al. |
| 2004/0170968 A1 | 9/2004 | Lizardi |
| 2004/0209298 A1 | 10/2004 | Kamberov et al. |
| 2004/0209299 A1 | 10/2004 | Pinter et al. |
| 2005/0019762 A1 | 1/2005 | Olek |
| 2005/0153296 A1 | 7/2005 | Berlin |
| 2005/0196792 A1 | 9/2005 | Fodor et al. |

FOREIGN PATENT DOCUMENTS

| WO | WO 99/10540 A | 3/1999 |
| WO | WO 01/77373 A | 10/2001 |
| WO | WO 02/46452 A | 6/2002 |
| WO | WO 03/080862 A | 10/2003 |
| WO | WO 03/080863 A | 10/2003 |
| WO | WO 03/087390 A | 10/2003 |
| WO | WO 2004/081183 A | 9/2004 |
| WO | WO 2004/081225 A | 9/2004 |

OTHER PUBLICATIONS

Barany, "Genetic disease detection and DNA amplification using cloned thermostable ligase," *Proc. Natl Acad. Sci. USA*, 88: 189-193 (Jan. 1991).
Barker et al., "Two methods of whole-genome amplification enable accurate genotyping across a 2320-SNP linkage panel," *Genome Res.*, 14: 901-907 (May 2004).
Dean et al., "Comprehensive human genome amplification using multiple displacement amplification," *Proc. Natl. Acad. Sci. USA*, 99: 5261-5266 (Apr. 16, 2002).
Del Gaudio et al., "Characterization of a new variant DNA (cytosine-5)-methyltransferase unable to methylate double stranded DNA isolated from the marine annelid worm *Chaetopterus variopedatus*," *FEBS Lett.*, 460 (2): 380-384 (Oct. 29, 1999).
Fire et al., "Rolling replication of short DNA circles," *Proc. Natl Acad. Sci. USA*, 92: 4641-4645 (May 9, 1995).
Gitan et al., "Methylation-specific oligonucleotide microarray: a new potential for high-throughput methylation analysis," *Genome Res.*, 12: 158-164 (Jan. 2002).
Gonzalgo et al., Rapid quantitation of methylation differences at specific sites using methylation-sensitive single nucleotide primer extension (Ms-SNuPE), *Nucl. Acids Res.*, 25: 2529-2531 (Jun. 15, 1997).
Herman et al., "Methylation-specific PCR: a novel PCR assay for methylation status of CpG islands," *Proc. Natl. Acad. USA*, 93: 9821-9826 (Sep. 3, 1996).
Lage et al., "Whole genome analysis of genetic alterations in small DNA samples using hyperbranched strand displacement amplification and array-CGH," *Genome Res.*, 13, 294-307 (Feb 2003).
Rand et al., "Conversion-specific detection of DNA methylation using real-time polymerase chain reaction (ConLigh-MSP) to avoid false positives," *Methods*, 27(2): 114-120 (Jun. 2002).

* cited by examiner

*Primary Examiner*—Teresa E Strzelecka
(74) *Attorney, Agent, or Firm*—Leydig, Voit & Mayer, Ltd.

(57) ABSTRACT

A method for copying the methylation patterns of molecules of genomic DNA (MGD) during isothermal amplification of the MGD comprising obtaining MGD, copying the methylation patterns of the MGD using a DNA methylation-maintenance enzyme, while isothermally amplifying the MGD using a DNA polymerase with strand displacement activity, under conditions that simultaneously promote activity of the DNA methylation-maintenance enzyme and the DNA polymerase; a method for copying the methylation patterns in double-stranded DNA molecules during isothermal amplification of the DNA molecules comprising obtaining DNA molecules, contacting the DNA molecules with transposable elements and an enzyme, which can randomly insert the transposable elements into the DNA molecules, copying the methylation patterns of the DNA molecules using a DNA methylation-maintenance enzyme, while isothermally amplifying the DNA molecules using a DNA polymerase with strand displacement activity, under conditions that simultaneously promote activity of the DNA methylation-maintenance enzyme and the DNA polymerase; a buffer comprising a divalent ion, deoxynucleotide triphosphates (dNTPs), primers, and S-adenosyl-methionine (SAM); and a composition comprising a DNA methylation-maintenance enzyme, a DNA polymerase with strand displacement activity, and the buffer.

13 Claims, No Drawings

METHODS OF COPYING THE METHYLATION PATTERN OF DNA DURING ISOTHERMAL AMPLIFICATION AND MICROARRAYS

CROSS REFERENCE TO RELATED APPLICATIONS

This application claims the benefit of U.S. Provisional Pat. App. No. 60/671,193, filed on Apr. 14, 2005, which is hereby incorporated by reference in its entirety.

TECHNICAL FIELD OF THE INVENTION

The present invention relates to a method for copying the methylation patterns in DNA molecules during isothermal amplification of the DNA, and a buffer and a composition for use in such a method.

BACKGROUND OF THE INVENTION

The epigenetic modification of DNA is essential for normal development and differentiation in higher eukaryotes (reviewed in Robertson, Nat. Rev. Genet. 6(8): 597-610 (2005)). Mammalian DNA is modified at CpG residues through the addition of a methyl group to the cytidine nucleotide. Clusters of CpG dinucleotides are found in the promoter and 5' regions of genes, and are referred to as CpG islands. Approximately half of mapped human genes have a CpG island upstream or within the 5' end of the transcript. Methylation of gene-associated CpG islands is correlated with reduced expression or complete silencing of the corresponding gene (reviewed in Baylin, Nat. Clin. Pract. Oncol. Suppl. 1: S4-11 (2005)).

The ability to detect methylation patterns in DNA is desirable in many applications, such as in the context of diagnosis of diseases, such as cancer. Over the last 20 years, analysis of methylation patterns derived from tumor tissues has identified aberrant methylation (hypomethylation and/or hypermethylation) of CpG islands as a common event in most cancers (Lumd et al., Genes Dev. 18(19): 2315-2335 (2004); Baylin, Nat. Clin. Pract. Oncol. Suppl. 1: S4-11 (2005); and Laird, Hum. Mol. Genet. Spec. No. 1: R65-76 (2005)). This aberrant methylation represents a novel DNA modification, which is not normally present in normal tissue and may not be present in the organism. As such, the detection of aberrant methylation in tissue samples or in DNA recovered from bodily fluids is an indication of the presence of cancer. Methylation offers a rich target for diagnostics, given the large number of sequences that are affected. In fact, a CpG island does not need to be associated with the promoter or the 5' end of a transcript to be useful in cancer diagnosis. The only requirement is for a sequence containing one or more CpG dinucleotides to exhibit a change in methylation during the development of a disease. Since both hypo- and hyper-methylation have been observed in cancer, tests can be developed to detect either/both methylation states in the diagnosis of cancer as well as other disease states.

There are a number of obstacles that need to be overcome in order to utilize successfully the detection of DNA methylation in diagnostic applications. First, the amount of DNA recovered from bodily fluids, such as plasma or urine, is usually only a few nanograms per milliliter (Jahr et al., Cancer Res. 61(4): 1659-1665 (2001); and Anker et al., Cancer Metastasis Rev. 18(1): 65-73 (1999)), which is insufficient for the analysis of a multitude of markers. Some cancer patients can exhibit higher levels of DNA in their bodily fluids, while others have amounts comparable to those isolated from normal individuals. While the amount of DNA can be increased by extracting a larger sample, there is a limit as to the volume that can be obtained and analyzed in a clinical setting.

Second, circulating DNA can be derived from both normal and diseased tissues. When nucleic acids are isolated from tissue samples and cell lines, the purified DNA is representative of the sample from which it was isolated. In normal tissues, genomic markers are equally represented in the purified DNA. The same may not be true for circulating DNA. The amount of circulating DNA derived from cancer cells can be very small and can represent as little as 3% of the total (Jahr, supra). In addition, the minimal amount of circulating DNA may not contain an equal representation of all abnormally methylated CpG islands present in the tumor.

Third, circulating cancer DNA can be derived from apoptotic and necrotic cells and, therefore, can be degraded and/or severely fragmented. The DNA fragments can be as short as a single or few nucleosomes (about 150 bp or short multiples of 150 bp). Most CpG islands are longer than 250 bp and many are longer than 1 kb. Fragmentation of DNA into nucleosomes causes the majority of CpG islands to be cleaved into 2 or more segments.

Fourth, the DNA can be further degraded by the methods used to reveal the methylation pattern. The most common method involves the controlled treatment of DNA with sodium bisulfite (Frommer et al., PNAS 89: 1827-1831 (1992)), which preferentially deaminates unmethylated cytidines, resulting in a detectable sequence change. Bisulfite treatment is harsh and results in severe degradation and loss of DNA (Grunau et al., Nucleic Acids Res. 29(13): E65-5 (2001)).

Fifth, cancer detection requires the use of multiple markers (Yegnasubramanian et al., Cancer Res. 64(6): 1975-86 (2004)). Even more markers will be needed in cancer diagnostic assays from circulating DNA to achieve the sensitivity and specificity needed for clinical applications. Methylation analysis is further complicated by the heterogeneity of DNA methylation patterns in cancers which may differ between tumors derived from different tissues (Esteller, Cancer Res. 61(8): 3225-9 (2001)), and between tumors derived from the same tissue (Zhao, Cancer 104(1): 44-52 (2005)). Therefore, methylation-based cancer diagnosis requires the analysis of multiple CpG islands and multiple CG residues across the length of an island. Such analysis requires more DNA than is usually isolated from bodily fluids.

Given all of these limitations, the detection of CpG methylation from circulating DNA requires assays that are designed to improve the sensitivity of detection despite the fragmentation of the templates. There is a need for a method that preserves the methylation pattern of the DNA, while, at the same time, increasing the amount of the DNA, so that methylation patterns can be easily detected and used to diagnose diseases. In this regard, methods to amplify DNA are well-known in the art and generally fall under two broad categories: the polymerase chain reaction (PCR) and isothermal amplification (see various patents and published patent applications by Lizardi, such as U.S. Pat. Nos. 5,854,033; 6,124,120; 6,143,495; 6,210,884; 6,642,034; 6,280,949; 6,632,609; and 6,642,034; and U.S. Pat. App. Pub. Nos. 2003/0032024; 2003/0143536; 2003/0235849; 2004/0063144; and 2004/0265897, each of which is specifically incorporated herein by reference in its entirety).

PCR requires the use of thermostable polymerases and primers flanking regions of interest and repeated cycling between temperatures that allow for denaturing of the DNA, annealing of primers to complementary DNA, and replicating of targeted sequences. When the primers used are random or partially random, they anneal to homologous sites randomly across the entire genome, leading to whole genome amplification.

Isothermal amplification, on the other hand, relies on the ability of mesophilic and thermophilic polymerases to displace existing DNA strands during DNA replication. When multiple primers, which flank regions of interest, are added to the amplification mix, multiple strand displacements lead to the generation of numerous overlapping fragments corresponding to the regions of interest. When the DNA is circular, strand displacement results in amplification by rolling circles. When random primers are used, multiple strand displacements lead to amplification of the whole genome. In addition, primers, which contain unique and random sequences, can be used to introduce unique "tags" across the genome. The advantage of isothermal amplification is the ability to perform the entire amplification process under constant temperature.

Methods, which combine PCR and isothermal amplification, also have been described (U.S. Pat. Nos. 6,777,187; and 6,828,098; and U.S. Pat. App. Nos. 2004/0209298; 2005/0032104; and 2006/0068394, each of which is specifically incorporated herein by reference in its entirety). Makarov et al. (U.S. Pat. App. No. 2005/0202490, which is specifically incorporated herein by reference in its entirety) describes the use of such methods in combination with methylation-sensitive restriction enzymes to study the methylation pattern of DNA.

All DNA amplification methods, however, are disadvantageous in that they fail to copy the methylation pattern of the DNA. Thus, in and of themselves, they are useless for the detection of methylation in the diagnosis of disease.

Lopez et al. (U.S. Pat. No. 6,514,698 and Int'l Pat. App. Pub. No. WO 99/10540) discloses using DNA methyltransferases to introduce methylation patterns (i.e., de novo methylation) into amplified DNA to detect variations, mutations or polymorphisms in DNA in an effort to genotype the DNA. Lopez et al. discloses that the use of DNA methyltransferases as proposed overcomes many of the disadvantages of the use of restriction endonucleases to genotype DNA. Lopez et al. does not teach, let alone even suggest, that DNA methyltransferases could be used to copy existing methylation patterns, while amplifying DNA, in an effort to assess abnormal methylation in the diagnosis of disease.

Berlin et al. (Int'l Pat. App. Nos. PCT/EP03/03104 and PCT/EP03/03105, Int'l Pub. Nos. WO 03/080862 and WO 03/080863, which are specifically incorporated herein by reference in their entireties) discloses that mass spectrometry can be used to analyze the methylation patterns of preselected regions (or targets) of amplified genomic nucleic acids, which have been isolated from a biological sample, and sequentially (i) copied and (ii) methylated repeatedly until the desired amount of nucleic acid is obtained. Berlin et al. discloses that ligase chain reaction, polymerase chain reaction, polymerase reaction, or rolling circle replication can be used to copy the preselected regions (or targets). However, while the methylation patterns of the preselected regions (or targets) of the genomic nucleic acids are maintained with sequential copying and methylation reactions, Berlin et al. does not enable maintenance methylation under isothermal amplification conditions when rolling circle replication is used or when polymerases with strand-displacement capabilities are used. The only conditions taught (pg. 29, lines 20-24) by Berlin et al. for methylation reaction with DNA methyltransferase 1 (DNMT-1) do not enable the polymerization reaction with a strand-displacing polymerase. Furthermore, Berlin et al. fails to address the de novo methylation that is introduced into the sample when DNMT-1 is used to copy the methylation pattern. The de novo activity of DNMT-1 introduces methylation on templates, which are not methylated in the original sample. This activity mimics the presence of a small amount of methylated templates as would be expected when circulating DNA from patients with early onset of disease is analyzed. The methodology of Berlin et al. will not enable the early detection of disease, such as cancer, because the amount of DNA that is derived from circulating DNA is minute, often representing less than 5% of the total DNA.

Fodor et al. (U.S. Pat. App. Pub. No. US 2005/0196792, which is specifically incorporated herein by reference in its entirety) discloses the use of a strand-displacing polymerase and a DNA methyltransferase to copy the methylation pattern from the parent strand into the daughter strand before the daughter strand is displaced during replication. The only conditions taught (para. [0076]) by Fodor et al. for methylation reaction with the DNMT-1 do not enable the polymerization reaction with a strand-displacing polymerase. Furthermore, like Berlin et al., Fodor et al. fail to address the de novo methylation that is introduced into the sample when DNMT-1 is used to copy the methylation pattern. Consequently, Fodor et al. also will not enable the early detection of disease, such as cancer. Furthermore, while Fodor et al. may claim variant forms of human and mouse DNMT-1s, Fodor et al. does not teach, let alone suggest, how to obtain such variant forms.

In view of the above, there remains a need for a method that enables copying of the methylation patterns of DNA molecules during isothermal amplification using a DNA methylation-maintenance enzyme and a DNA polymerase with strand displacement activity under conditions that simultaneously promote activity of the DNA methylation-maintenance enzyme and the DNA polymerase with strand displacement activity. Preferably, the method provides a level of sensitivity to detect methylation patterns in DNA available only in very limited quantities. The present invention seeks to provide such a method. This and other objects and advantages, as well as additional inventive features, will become apparent from the detailed description provided herein.

BRIEF SUMMARY OF THE INVENTION

The present invention provides a method for copying the methylation patterns of molecules of genomic DNA (MGD) during isothermal amplification of the MGD. The method comprises obtaining MGD, copying the methylation patterns of the MGD using a DNA methylation-maintenance enzyme, while isothermally amplifying the MGD using a DNA polymerase with strand displacement activity under conditions, which simultaneously promote activity of the DNA methylation-maintenance enzyme and the DNA polymerase with strand displacement activity, and, optionally, purifying the MGD as necessary to enable further manipulation.

The present invention also provides a method for copying the methylation patterns in double-stranded DNA molecules during isothermal amplification of the DNA molecules. The method comprises obtaining DNA molecules, contacting the DNA molecules with transposable elements and an enzyme, which can randomly insert the transposable elements into the DNA molecules, copying the methylation patterns of the DNA molecules using a DNA methylation-maintenance enzyme, while isothermally amplifying the DNA molecules using a DNA polymerase with strand displacement activity, under conditions that simultaneously promote activity of the DNA methylation-maintenance enzyme and the DNA polymerase with strand displacement activity, and, optionally, purifying the DNA molecules as necessary to enable further manipulation; whereupon the DNA molecules are amplified and their methylation patterns are copied.

A buffer comprising a divalent ion, deoxynucleotide triphosphates (dNTPs), primers, and S-adenosyl-methionine (SAM) is provided. Similarly, a composition comprising a DNA methylation-maintenance enzyme, a DNA polymerase with strand displacement activity, and the just-described buffer is also provided.

DETAILED DESCRIPTION OF THE INVENTION

The present invention provides a method for copying the methylation patterns of MGD during isothermal amplification of the MGD. The method is advantageous inasmuch as it allows the analysis of a sufficient number of markers from limited quantities of DNA, thereby enabling the diagnosis of disease. Amplification of all DNA molecules present in a sample is possible in accordance with the teachings of the present invention, as is the amplification of very small quantities of degraded/fragmented DNA molecules, such as that which are recovered from bodily fluids.

The method comprises (i) obtaining MGD, (ii) copying the methylation patterns of the MGD using a DNA methylation-maintenance enzyme, while isothermally amplifying the MGD using a DNA polymerase with strand displacement activity, under conditions that simultaneously promote activity of the DNA methylation-maintenance enzyme and the DNA polymerase with strand displacement activity. The conditions that simultaneously promote activity of the DNA methylation-maintenance enzyme and the DNA polymerase with strand displacement activity comprise the presence of a buffer comprising a divalent ion, dNTPs, primers, and SAM. The method results in amplified DNA molecules in which the methylation patterns have been copied from the original DNA molecules in the sample. In view of the above, step (ii) can further comprise:

(i') mixing the MGD and the primers, wherein either of (a) the MGD or (b) the MGD and the primers are optionally denatured before or after mixing, (ii') incubating the mixture of (i') at a temperature from at least about 0° C. to about 75° C. for a sufficient amount of time to allow annealing of the primers to the MGD, (iii') equilibrating the mixture of (ii') to an optimal temperature for methyltransferase activity, (iv') adding a buffer, which comprises a divalent ion, dNTPs, primers, and SAM, and which is already equilibrated to the optimal temperature of (iii'), and simultaneously with or sequentially to adding the buffer, adding a DNA methylation-maintenance enzyme and a DNA polymerase with strand displacement activity, to the mixture of (iii'), and (v') incubating the mixture of (iv') at an optimal temperature for methyltransferase activity for a sufficient amount of time to allow methylation-coupled amplification of the MGD until a desired amount is obtained.

Any suitable sample of MGD can be used in the present inventive methods. For example, genomic DNA can be obtained from any bodily fluid, such as plasma, urine, saliva, or circulating cells (referred to herein as "circulating DNA"), from fresh tissues, such as those obtained from biopsies or during surgery, and preserved tissues, such as paraffin-embedded tissues. Circulating tumor cells can be obtained from bodily fluids using any suitable method to separate tumor cells from normal cells. For example, tumor cells can be enriched from blood samples using antibodies to cell-surface antigens, which are present on tumor cells and absent on white blood cells. A commercially available kit, Dynabeads Epithelial Enrich (Invitrogen, Carlsbad, Calif.), uses antibody-coated magnetic beads to separate epithelial cells from normal white blood cells. When a biological sample is available in very limiting quantities (e.g., a few cells), such as in the case of circulating cells, it is not necessary to purify the DNA prior to methylation-coupled isothermal amplification. The cells can be lysed under denaturing conditions to release the DNA, and enzymes and buffers can be added to copy the methylation pattern while isothermally amplifying the DNA.

DNA optionally can be purified prior to any enzymatic manipulation. Methods to extract DNA from tissue samples are known in the art and include standard proteinase K digest, phenol/chloroform extraction, and ethanol precipitation (*Short Protocols in Molecular Biology*, 5$^{th}$ ed., Ausubel et al., eds., Wiley & Sons, Inc. (2002); and Methods in Enzymology, V152 (Academic Press, Elsevier, Inc., Burlington, Mass. (1987)). Alternative methods include purification using silica or anion exchange chromatography. Many commercial kits are available for DNA extraction using both of these methods (Qiagen (Valencia, Calif.), Promega (Madison, Wis.), and Eppendorf (Westbury, N.Y.), among others). These kits are also suitable for the isolation of DNA from urine sediments and plasma samples. For paraffin-embedded samples, the paraffin is first removed using an organic solvent, such as xylene. The DNA then can be extracted using any of the methods described above.

The DNA can be double-stranded, single-stranded, or a combination thereof. The DNA can be largely intact or fragmented, in which case the fragments can have shorter strands and longer strands. When the DNA is completely or partially double-stranded, the method optionally further comprises contacting the DNA with transposable elements and an enzyme, which can randomly insert the transposable elements into the DNA, whereupon the DNA comprises the randomly inserted transposable elements. The inserted transposable elements provide a known sequence that can be used to initiate methylation-coupled whole genomic amplification. The frequency of the insertion events can be controlled by varying the amount of transposon DNA added to the transposition reaction. One or more primers complementary to one or both strands of the transposon can be added to the methylation-coupled amplification to allow for priming events to occur with equal efficiency along the length of all DNA fragments. Randomly inserted transposons can also help to destabilize secondary structure in high GC regions and improve sequence representation.

By "transposable element" is meant any DNA fragment, whether naturally occurring, recombinant, or synthetic, that can be inserted into DNA at random. The transposable element can have mosaic ends, i.e., the two copies of the short sequence that defines the two ends of the transposable element may differ slightly but are still bound by a transposase. Typically, transposable elements range in length from about a few hundred base pairs (bp) to over 20 kilobase pairs (kb). Transposable elements having a length from about 50 bp to about 20 kb are preferred, whereas transposable elements having a length from about 100 bp to about 5 kb are more preferred, and transposable elements having a length from about 250 bp to about 2.5 kb are most preferred. Any enzyme that can randomly insert transposable elements into the DNA can be used in the method. Examples of suitable enzymes include, but are not limited to, a transposase. A kit to introduce transposons into target DNA, such as EZ-Tn5<Kan-2> or EZ-Tn5<Tet-1>, is commercially available from Epicentre (Madison, Wis.).

A transposable element can be engineered in vitro to contain internal segments, which are only partially complementary, and as such create open regions or bubbles within the transposon, which can be used for primer annealing without any denaturation of the DNA sample. Such a transposon can be generated in vitro by first modifying an internal portion of the transposon using in vitro mutagenesis to create a "mutant" with an internal sequence that differs completely or is partially homologous to the "wild-type" sequence. Using linear PCR amplification, single-stranded wild-type and mutant transposons are amplified. Annealing of the complementary strands results in the generation of a double-stranded transposon with an internal bubble that can be used for the transposition reaction.

In view of the above, the present invention also provides a method for copying the methylation patterns of double-stranded DNA molecules during isothermal amplification of the DNA molecules, which method comprises:

(i) obtaining DNA molecules, (ii) contacting the DNA molecules with transposable elements and an enzyme, which can randomly insert the transposable elements into the DNA molecules, whereupon the DNA molecules comprise the randomly inserted transposable elements, (iii) copying the methylation patterns of the DNA molecules using a DNA methylation-maintenance enzyme, while isothermally amplifying the DNA molecules using a DNA polymerase with strand displacement activity, under conditions that simultaneously promote activity of the DNA methylation-maintenance enzyme and the DNA polymerase with strand displacement activity, and, optionally, (iv) purifying the DNA molecules as necessary to enable further manipulation, When the DNA is completely or partially double-stranded, the method can further comprise denaturing the sample of DNA prior to or during step (ii). Various methods of denaturing DNA are known in the art. For example, DNA can be denatured by heating at high temperatures for 5 to 10 min in water or TE buffer, or DNA can be denatured by adding NaOH or KOH and incubating for 5 to 10 min at room temperature, followed by neutralization.

When the DNA is single-stranded and comprises fragments, the method can further comprise contacting the DNA with an enzyme that ligates single-stranded nucleic acids under reaction conditions that promote ligation, optionally in the presence of a polynucleotide kinase. Polynucleotide kinases and ligases are known in the art and are commercially available. For example, T4 polynucleotide kinase and T4 RNA ligase are available from many suppliers (New England Biolabs (NEB; Beverly, Mass.), Invitrogen, Roche (Indianapolis, Ind.), Epicentre, and Promega). The reactions are performed according to the suppliers' conditions. Additionally, a single-stranded oligonucleotide can be added to the ligation reaction to introduce a unique sequence into the target DNA that may facilitate the amplification and detection reactions.

When the DNA is double-stranded and comprises fragments, the method can further comprise contacting the DNA with an enzyme that generates blunt ends or compatible ends on the fragments under reaction conditions that promote the generation of such ends. The blunt ends can be generated by extending the shorter strands of the fragments, by shortening the longer strands of the fragments, or a combination thereof, optionally in the presence of a polynucleotide kinase.

Any DNA polymerase with proofreading capabilities can be used to generate blunt/compatible ends. Examples of such polymerases include, but are not limited to, Klenow polymerase, *E. coli* DNA polymerase, and T4 DNA polymerase. Reaction conditions are known in the art (see, e.g., Ausubel et al., supra; Methods in Enzymology, V152 (Academic Press, Elsevier, Inc., Burlington, Mass. (1987)). If polynucleotide kinase is also present, then the reaction buffer is supplemented with ATP. The method can further comprise contacting the DNA with an enzyme that ligates double-stranded nucleic acids (e.g., T4 DNA ligase) optionally in the presence of a double-stranded linker. Desirably, the DNA is contacted with the enzyme under conditions that promote ligation, optionally in the presence of a polynucleotide kinase. Ligation of a population of DNA fragments yields linear concatenated DNA fragments and circular concatenated DNA fragments. The ratio of linear to circular molecules will vary, based on the concentration of the DNA in the sample. Whole genomic amplification proceeds by multiple strand displacements. In case of circular DNA molecules, multiple strand displacements result in a rolling circle amplification.

The method can further comprise the ligation of an adapter to the blunt-ended DNA to generate a DNA molecule without free ends (see, e.g., Weissman et al., U.S. Pat. No. 6,576,448). The adapter is a single oligonucleotide comprising 5' and 3' complementary segments separated by a unique segment. Primers designed based on the unique segment of the adapter can be used to initiate DNA amplification.

Any suitable DNA methylation-maintenance enzyme can be used in the context of the present inventive method. The DNA methylation-maintenance enzyme can be derived from a eukaryote. As used herein the phrase "derived from" means isolation of the protein from an organism or recombinant production in accordance with methods known in the art. Two classes of DNA methyltransferases have been identified so far in lower and higher eukaryotes (reviewed in Ponger, Mol. Biol. Evol. 22(4): 1119-1128 (2005); and Bestor, Hum. Mol. Genet. 9(16): 2394-2402 (2000)). The first class includes the human Dnmt2, Dnmt3a, and Dnmt3b and catalyzes the de novo methylation of CpG residues. The second class is responsible for the maintenance of DNA methylation at CpG residues following replication. This activity is carried out by the human DNA DNMT-1 enzyme, but similar enzymes have been cloned from lower eukaryotes, such as the sea urchin, the annelid worm *Chaetopterus variopedatus*, and the fungus *Neurospora crassa* (Aniello et al., Gene 178: 57-61 (1996); del Gaudio et al., FEBS Letters 460: 380-384 (1999); and Kouzminova et al., Embo J. 20: 4309-4323 (2001)). Thus the eukaryote, from which the DNA methylation-maintenance enzyme can be derived, can be an Annelida, such as a Polychaeta, in particular a marine annelid worm, e.g., *Chaetopterus variopedatus*. Alternatively, the Annelida can be a Clitellata, such as an earthworm. The eukaryote can be a fungus, such as *Neurospora crassa*. Other suitable eukaryotes include a human, a mouse, a rat, a chicken, a cow, a pig, or a plant.

Conditions, which promote the maintenance of the methylation pattern of hemi-methylated DNA by the human DNMT-1, are provided by NEB. Commercially available human DNMT-1 enzyme also can perform the methylation reaction under conditions that promote amplification when DNA polymerase buffer is supplemented with SAM.

DNMT-1 exhibits de novo methylation activity in vitro. The degree of specificity of mouse and human DNMT-1 for hemi-methylated substrates was estimated to range between 2- and 50-fold using oligonucleotide substrates (Fatemi et al., J. Mol. Biol. 309: 1189-1199 (2001); Pradham et al., J. Biol. Chem. 274: 33002-33010 (1999); and Tollefsboll et al., J. Mol. Biol. 269: 494-504 (1997)). Furthermore, it has been shown that the addition of methylated DNA reduces the specificity of DNMT-1 towards hemi-methylated substrates (Bacolla et al., J. Biol. Chem. 279: 48350-48359 (1999); and Christman et al., PNAS 92: 7347-7351 (1995)). When both unmethylated and hemi-methylated substrates were present in the same sample, DNMT-1 has a 12-fold preference for the hemi-methylated substrate, which was preferentially and processively methylated (Goyal et al., NAR 34(4): 1182-1188 (2006)). However, the de novo methylation level on the unmethylated substrate was 5%. The de novo methylation presents a challenge for the replication of the DNA methylation pattern in diagnostic assays, especially when circulating DNA is being analyzed. It could result in an increase in false positives, therefore reducing the specificity and the utility of the diagnostic assay.

For methylation-coupled amplification, it is preferred that the DNMT-1 enzyme lacks activity towards unmethylated substrates. To date, only the enzyme from the annelid worm has been reported to lack activity towards unmethylated substrates. The enzyme can be purified from the annelid worm *Chaetopterus variopedatus* (del Gaudio et al., FEBS Letters 460: 380-384 (1999)). It is preferred that the annelid DNMT-1 is obtained from recombinant sources. The gene can be cloned from a cDNA expression library made with RNA isolated from the annelid worm using antibodies towards the sea urchin DNMT-1. It also can be cloned using the sea urchin DNMT-1 gene as a probe to screen a polychaeta cDNA library. Alternatively, fragments of the DNMT-1 transcript can be amplified using primers designed from conserved regions of the protein, especially in the catalytic domain, which is highly conserved in prokaryotes and eukaryotes. The primers can contain one or more degenerate positions because the majority of amino acids are encoded by multiple codons. Examples of such primers include WDNMT-F1 (TTCARCACNYTSATHCCAMTGGTG; SEQ ID NO: 1), WDNMT-F2 (ATHCCMTGGTGYCTDCCHCA; SEQ ID NO: 2), WDNMT-F3 (AACHGVCAYAAY-MACTGGGCBGG; SEQ ID NO: 3), WDNMT-F4 (GANT-GYTTYCAYCARGCNGGNAT; SEQ ID NO: 4) WDNMT-F5 (ATGGGNTAYCARTCNACNTTYGG; SEQ ID NO: 5) WDNMT-F6 (TAYCTSAGCTACTGTGACTAYTAC; SEQ ID NO: 6), WDNMT-F7 (TGGARAATGTCCG-KAACTTTGTATC; SEQ ID NO: 7), WDNMT-R1 (AABC-CYTGNGABCGNGCRCAYTCCC; SEQ ID NO: 8), WDNMT-R2 (TGGGACGGHTTCTTCAGYACHAC; SEQ ID NO: 9), WDNMT-R3 (GCRCACTCCCTSACRCTCAC-CAC; SEQ ID NO: 10), and WDNMT-R4 (GTDGTRCT-GAAGAADCCGTCCCA; SEQ ID NO: 11). These primers can be used in combinations in RT-PCR reactions using reverse-transcribed mRNA from the annelid worm as a template followed by cloning, sequencing, and sequence homology analysis to identify fragments of DNMT-1. Nested PCR also can be used to reduce the complexity of the amplified products and increase the likelihood of identifying DNMT-1. Alternatively, these primers can be used in PCR reactions to amplify the 5' or 3' end of the transcripts (RACE amplification) if the mRNA is reverse-transcribed with the addition of appropriate linkers. Kits are available to facilitate RACE amplification (e.g., GeneRacer kit, which is available from Invitrogen). Nested PCR also can be used to reduce the number of amplification products that require analysis. Alternatively, primers with minimal or no degeneracies can be designed from the sea urchin DNMT-1 transcript and used in RT-PCR or RACE amplification under less stringent conditions to amplify fragments of the transcript. The primers can be used to amplify fragments of the DNMT-1 gene from genomic DNA using methods that are known in the art (e.g., vectorette PCR). Other methods are also suitable and are well-known in the art.

Alternatively, methylases from other organisms that can maintain methylation at CpG dinucleotides can be cloned and tested to identify an enzyme lacking de novo activity. A large number of DNA methylases, which have been described in the literature, are suitable candidates, including a DIM2 methylase from the fungus *Neurospora crassa* that can maintain methylation at CpN residues (Ponger et al., Mol. Biol. Evol. 22(4): 1119-1128 (2005); and Kouzminova et al., E.U. Embo J. 20: 4309-4323 (2001)).

DNMT-1 enzymes from eukaryotes also can be modified or mutagenized to reduce or eliminate their activity towards unmethylated substrates (i.e., de novo methylation activity). For example, random mutagenesis can be performed on the regulatory N-terminal domain of the human DNMT-1, and the resulting fragments cloned into an expression vector to produce mutagenized full-length recombinant proteins that can be screened for lower or absent activity towards unmethylated DNA. Kits for the performance of random mutagenesis are commercially available (e.g., Diversify Random Mutagenesis Kit, which is available from Clontech (Mountain View, Calif.)).

Alternatively, the wild-type enzymes can be used for the methylation-coupled amplification reaction in conjunction with a method of analysis that permits the differentiation between true methylation and artifacts introduced by the de novo activity of the enzyme. Conditions that minimize the de novo activity of the enzyme are established experimentally for each batch of DNMT-1 enzyme as follows: the level of de novo DNA methylation is measured using control DNA, which is not methylated at regions of interest, such as DNA isolated from blood or lymphoblastoid cell lines. Additionally, the control DNA is mixed with increasing amounts of template DNA, which carries methylation at sites of interest to mimic the DNA isolated from bodily fluids. The ratio of control to sample DNA can range from 200:1 to 1:1. The buffer composition can be modified (e.g., varying magnesium and salt concentrations, or adding glycerol or DMSO). The length of the reaction and the ratio of DNMT-1 to DNA polymerase can be varied to identify the best combination for amplification that minimizes background "de novo" methylation.

The level and pattern of methylation are established for each marker of interest in each control reaction described above using DNA templates, which are fully methylated, fully unmethylated, or partially methylated. Unmethylated templates can be generated by multiple strand displacement of human genomic DNA using GGGN6 for primers. Fully methylated DNA can be generated by treatment of human genomic DNA with SssI methylase (NEB, Beverly, Mass.) according to conditions provided by the supplier. Partially methylated DNA can be isolated from tumor tissues or cell lines derived from tumors. For each CpG island, the methylation status of at least 12 CpG dinucleotides is determined. Optionally, the methylation status of all CpGs in an island is determined. The analysis of multiple CpGs within each island and the analysis of a multitude of markers are important because DNMT-1 methylates hemi-methylated DNA processively and non-methylated DNA in a distributive manner. This analysis provides experimental conditions and methylation patterns that differentiate between de novo methylation introduced by the enzyme and true maintenance methylation of hemi-methylated DNA.

Protein (such as proliferating cell nuclear antigen (PCNA), and methyl-CpG binding domain proteins (MBD), such as MBD2 and MBD3 (Kelman et al., Trends Biochem. Sci. 23: 236-238 (1999); and Tatematsu et al., Genes to Cells 5: 677-68 (2000)), which normally interacts with DNMT-1 at replication foci, can be added to the amplification reaction. The input DNA also can be diluted with foreign DNA (e.g., bacterial DNA) to minimize the number of de novo methylation events on the MGD. The methylation-coupled amplification yields up to tens of micrograms from as little as a few picograms of starting DNA. The presence of the foreign DNA does not interfere with the analysis of methylation of the MGD.

Some sequences may not amplify under the most commonly used conditions due to secondary structure and high GC content. Secondary structure can be destabilized by ssDNA binding proteins (ssDNABP). Examples of such ssDNABP include, but are not limited to, T4 gene 32 protein (NEB) and the *E. coli* single-stranded DNA binding protein SSB (Epicentre).

Any suitable DNA polymerase can be used to amplify DNA in the context of the present inventive methods. Desirably, the DNA polymerase has strand displacement activity. Examples of such polymerases include, but are not limited to, Klenow exo-polymerase, sequenase (modified T7 polymerase), and Bst polymerase (large fragment).

The method can be performed under any suitable conditions. Desirably, the conditions simultaneously promote activity of the methylation-maintenance enzyme and the DNA polymerase. Such conditions comprise the presence of a buffer comprising a divalent ion, dNTPs, primers, and SAM. A divalent ion can be derived from any suitable salt that promotes DNA polymerase activity. A preferred divalent ion is the divalent cation magnesium. Magnesium is preferably derived from magnesium chloride or magnesium sulfate. It is preferred that the divalent ion, e.g., divalent cation, such as magnesium, is present in the reaction buffer at a concentration between about 0.1 mM and about 100 mM. It is more preferred that the concentration is between about 1 mM and about 25 mM. It is most preferred that the concentration is between about 2 mM and about 15 mM. It is also preferred that the dNTP concentration is between about 10 µM and about 10 mM. It is more preferred that the dNTP concentration is between about 30 µM and about 5 mM. It is most preferred that the dNTP concentration is between about 50 µM and about 2 mM. It is also preferred that the SAM concentration is between about 1 µM and about 500 µM. It is more preferred that the SAM concentration is between about 50 µM and about 250 µM. It is most preferred that the SAM concentration is about 160 µM. It is also preferred that additional aliquots of SAM are added to the methylation-coupled amplification reaction, if the incubation time is over 3 hours.

The primers can be random, specific, a combination thereof, or hybrids containing a unique portion and a random portion. When the primer is random, the primer is preferably from about 6 to about 30 nucleotides in length. When the primer is specific, the primer is preferably from about 12 to about 50 nucleotides in length and can include some degenerate bases. Specific primers can be complementary to repetitive sequences present within the genome, such as sine and line sequences, or they can be complementary to transposon sequences that were inserted in the DNA in vitro. Specific primers derived from unique sequences flanking the CpG islands can be added to the primer mix. However, these are not the most preferred primers for methylation-coupled amplification of circulating DNA because the concatemarized DNA is chimeric and such primers may not necessarily contribute to the amplification of the islands under study. Primers from within the CpG islands can be added to the mix; however, it is preferred that primers that enable the amplification of all templates present are used in methylation-coupled amplification. Examples of such primers include random or partially random primers N6, GGGN6, GGGN9, primers homologous to Alu repeats, AluF1 (cactgcactccagcct; SEQ ID NO: 12) and AluR1(ggtctcgatctcctg; SEQ ID NO: 13), and primers homologous to the Kan transposon (Epicentre), Kan2-F1 (caaagctctcatcaacc; SEQ ID NO: 14) and Kan2-R1 (gcaatgtaacatcagaga; SEQ ID NO: 15). If the primer contains a unique portion and a random portion, strand displacement amplification will result in the random introduction of the sequence of the unique portion into the genomic sequence, essentially mimicking the use of transposable elements. It is preferred that, when amplifying minute amounts of DNA, the total amount of primers added to the reaction mix is between 1 ng and 10 µg. It is more preferred that the amount of primers is between 5 ng and 5 µg. It is most preferred that the amount of primers is between 25 ng and 2 µg.

The primers can contain any number of modifications including, but not limited to, modified bases, such as phosphorothioate bases, deoxyinosine, and 5-nitroindole, and the incorporation of detectable labels, such as biotin, fluorescein, and other dyes.

In addition to the above, the methyl donor, SAM, can be labeled with a detectable label, such as a radioactive label. For example, $^3$H-labeled S-adenosylmethionine, which is available from Amersham (Piscataway, N.J.), can be used.

In view of the above, the methylation pattern of the DNA is preferably copied by simultaneously contacting the DNA with a DNA methyltransferase, which can copy the methylation pattern of hemi-methylated DNA, such as DNMT-1, and a DNA polymerase with strand displacement activity. Following methylation-coupled amplification, the DNA can be purified as necessary to enable further manipulation, or it can be used directly without purification, for example, in the sodium bisulfite treatment of the DNA. The extent of purification needed will be dictated in part by the particular manipulation to be performed. DNA purification methods are known in the art. For example, the DNA can be extracted with phenol/chloroform followed by ethanol precipitation. The amount of amplified DNA is substantially larger than the starting material and enables the analysis of the methylation pattern of a multitude of markers.

The method can further comprise analyzing the methylation pattern of the DNA. The methylation pattern can be revealed by contacting the DNA with a methylation-sensitive restriction enzyme under conditions that promote digestion of the DNA by the enzyme and detecting the results of the digestion. Examples of methylation-sensitive restriction enzymes are known in the art, as are the conditions that promote digestion of the DNA by the enzyme. Examples of such restriction enzymes include HpaII and HinP1I (NEB).

Alternatively, the methylation pattern can be revealed by contacting the DNA with an agent that preferentially deaminates unmethylated or methylated cytidines. Any suitable agent can be used. Examples of suitable agents include sodium bisulfite, which preferentially deaminates unmethylated cytidines resulting in sequence changes where thymines replace unmethylated cytidines in the DNA templates. Conditions for bisulfite treatment are known in the art (Frommer et al., PNAS 89: 1827-1831 (1992); and Shiraishi et al., DNA Research 11: 409-415 (2004)). Kits for bisulfite modification of DNA are commercially available (e.g., CpGenome Modification Kit, which is available from Chemicon (Temecula, Calif.)).

CpG islands vary in size from less than 250 bp to over 2 kb. The majority of the short islands are associated with repetitive sequences. CpG islands, which are located within a gene or its promoter, tend to be longer and may or may not contain repetitive sequences. A survey of 1,000 CpGs ranging in size from 350 bp to 2,850 bp showed an average length of 774 bp with an average of 9.89% CpG dinucleotides. Approximately one-third contained repetitive sequences that span over 10% of the length of the CpG island. In tumor tissues, DNA methylation is heterogeneous and may affect any combination of CpG dinucleotides. The analysis of the methylation status of multiple CpGs within an island is necessary to determine its methylation status. It is preferred that between 10 and 100% of CpGs are analyzed for each island. It is more preferred that at least 10 CpGs are analyzed for each island. It is also preferred that both strands of the CpG island are analyzed because the deamination reaction results in sequences, which are no longer complementary.

The results of the methylation-sensitive restriction digestion and the results of the bisulfite conversion can be detected by any suitable manner as known in the art. The sequence differences generated by bisulfite treatment between methylated and unmethylated templates can be analyzed using any method that is suitable for the detection of sequence polymorphisms in genomic DNA. For example, the results of the digest can be detected by Southern blot hybridization (Ausubel et al., supra), sequencing (Frommer et al., PNAS 89: 1827-1831 (1992)), methylation-specific PCR amplification (Herman et al., PNAS USA 93: 9821-9826 (1996); and U.S. Pat. Nos. 5,786,146 and 6,265,171, which are specifically incorporated herein by reference in their entireties), extension of oligonucleotides complementary to target DNA (Gonzalgo et al., Nucl. Acids Res. 25(12): 2529-2531 (1997); and U.S. Pat. No. 6,251,594, which are specifically incorporated herein by reference in their entireties), quantitative PCR (Rand et al., Methods 27: 114-120 (2002); and U.S. Pat. Nos. 6,331,393; 5,494,810; and 6,268,148, which are specifically incorporated herein by reference in their entireties), ligation-mediated amplification (Barany et al., PNAS USA 88(1): 189-193 (1991); and U.S. Pat. Nos. 5,494,810 and 6,268,148, which are specifically incorporated herein in their entireties), microarray analysis (Gitan, Methods 12: 158-164 (2001); Schumacher, NAR 34: 528-542 (2006); and U.S. Pat. App. Pub. Nos. 2003/0148326, 2003/0148327, and 2006/0068402, all of which are specifically incorporated herein by reference in their entireties), and mass spectrometry (Tost et al., Clin. Biochem. 38(4): 355-50 (2005); and U.S. Pat. App. Pub. No. 2005/0089904, which are specifically incorporated herein by reference in their entireties), for example.

When a multitude of CpGs and islands are to be analyzed, the methylation status can be determined by hybridization to an array of hybridization probes designed to encompass all combinations of methylated, partially methylated, and unmethylated oligonucleotide permutations derived from the sequence of the CpG islands. The CpG islands are amplified from the bisulfite-treated DNA using a plurality of primers using methods known in the art. Primers used for the amplification can be derived from sequences in the target templates that are devoid of CpG dinucleotides in order to amplify all templates equally. Alternatively, primers that are complementary to regions containing one or more CpG dinucleotides are used in order to reduce the complexity of the amplified product. Furthermore, multiple primer pairs for each target template can be utilized in the amplification reaction. The primers can carry a detectable label, or a label can be introduced during DNA amplification. Any suitable label can be used for this purpose including, but not limited to, radioactivity, fluorescent tags, and biotin or dioxygenin tags, all of which are commercially available (Amersham Biosciences; Invitrogen; Roche Applied Science). A detectable label is introduced into the bisulfite-treated DNA prior to microarray hybridization using methods known in the art (e.g., Amersham CyeDye ULS labeling kits Cy3-ULS and Cy5-ULS (Amersham Biosciences)).

The term "hybridization probes" refers to oligonucleotides or nucleic acids analogs or mimetics, such as peptide nucleic acids (PNA) (Nielsen et al., Science 254: 1497-1500 (1991)) and locked nucleic acids (LNA) (Vester et al., Biochem. 43(42): 13233-41 (2004); and U. S. Pat. No. 6,268,490).

The term "array" refers to a collection of molecules, which can be prepared synthetically or biosynthetically and tethered to a solid support, such as resin beads or silica chips. Methods to generate and analyze microarrays are well-known in the art (reviewed in Churchill, Nat. Genet. 32: 490-495 (2002); Schumacher, supra; The Tumor Analysis Best Practices Working Group, Nat. Reviews Genetics 5: 229-237 (2004); Quackenbush, Nat. Genet. 32: 496-501 (2002); and U.S. Pat. Nos. 5,807,522; 5,700,637; 5,744,305; 6,101,946; 6,753,145; and 6,858,394).

Accordingly, the present invention also provides a buffer comprising a divalent ion, dNTPs, primers, and SAM. The divalent ion, e.g., a divalent cation, such as magnesium, should be present in an amount that is suitable for the DNA polymerase reaction and the annealing of primers to template DNA. The amount of dNTPs should be optimal for the DNA polymerase reaction and can range from equilibrium to a large excess. The primers should be present in an amount to allow for amplification to proceed as desired; non-specific amplification, which can occur when there is a large excess of primers, and completion of amplification prior to methylation should be avoided. SAM should be present in an amount that is optimal for methyltransferase activity. In view of the foregoing, the present invention also provides a composition for methylation-coupled amplification of DNA comprising a DNA methylation-maintenance enzyme, a DNA polymerase with strand displacement activity, and the buffer. A suitable 1× buffer comprises 20 mM Tris, pH 7.8, 50-100 mM NaCl, 10 mM $MgCl_2$, 1 mM DTT, 160 µM SAM, 300 µM dNTPs, 100 ng of random primers GGGN6, DNMT-1, and either Klenow, Klenow exo-, Sequenase, or BST polymerase large fragment.

EXAMPLES

The following examples serve to illustrate the present invention and are not intended to limit its scope in any way.

Example 1

This example demonstrates methylation-coupled whole genomic amplification of the genomic DNA derived from human prostate cancer using random primers.

DNA was extracted from paraffin-embedded tumor tissues after microdissection using an H&E stained slide as a guide to enrich for tumor DNA. The tissue samples were extracted twice with 1 ml of xylene and twice with 1 ml of 100% ethanol and allowed to air dry. DNA was extracted using a standard proteinase (Methods in Enzymology, supra). The DNA was resuspended in TE8 buffer (10 mM Tris, pH 8.0, 1 mM EDTA). The concentration was determined by agarose gel electrophoresis and comparison with a concentration standard. The DNA was diluted to a final concentration of 10 ng/µl in TE8.

One µl of DNA (10 ng) and 50 ng of a partially random primer (GGGN6) were added to 7 µl $H_2O$. The DNA/primer mix was denatured at 94° C. for 5 min, and incubated at room temperature (RT) for 2 min before the addition of 1 µl of 10× buffer (1× NEB buffer 2: 50 mM NaCl, 10 mM Tris-HCl, pH 7.9, 10 mM $MgCl_2$, 1 mM dithiothreitol (DTT)). The DNA/primer mix was incubated at RT for an additional 15 min.

The amplification reaction was set up in a final volume of 30 µl, by adding the following reagents to give the final concentrations indicated below:

1× NEB buffer 2, 333 µM dATP, dCTP, dGTP, and dTTP, 160 µM SAM, and 10 ng/µl of bovine serum albumin (BSA). The reaction was equilibrated at 37° C. for 5 min, and DNMT-1 (0.167 units/µl), Klenow polymerase, and Klenow exo- were added to final concentrations of 0.167 units/µl (NEB or Epicentre).

The reaction was incubated at 37° C. for 16 hrs. An equal aliquot of SAM (equivalent to an additional 100 µM) was added to the reaction mix at 5 hrs and 10 hrs. An additional amplification reaction was performed as described above except that DNMT-1 was omitted from the mix. The resulting DNA lacked methylation and served as an unmethylated DNA control. The reaction was stopped by the addition of EDTA to a final concentration of 50 mM. A 5 µl aliquot was separated on a 0.8% agarose gel with DNA concentration standards and a molecular weight marker (1 Kb Ladder, Invitrogen). The majority of the amplified DNA migrated at or above the 10 kb band of the molecular weight marker with smearing observed towards the smaller bands. The amplified DNA was used directly for sodium bisulfite treatment without further manipulation. Alternatively, the DNA was extracted with phenol/chloroform and ethanol precipitated. The DNA was resuspended in 40 µl of TE8 and quantitated using a spectrophotometer.

As an alternative to heat treatment, the DNA was denatured using sodium or potassium hydroxide and neutralized as follows:

10 ng of DNA and 50 ng of GGGN6 primer in 5 µl of TE8 were denatured by the addition of an equal volume of freshly prepared 50 mM NaOH and incubated at RT for 5 min. The solution was neutralized by the addition of 5 µl of a freshly prepared solution of 50 mM Tris pH 7.9/50 mM HCl. Buffer, dNTPs, SAM, and enzymes were added as described above, and the reaction was allowed to proceed at 37° C. for 16 hrs.

Other DNA polymerases with strand displacement capabilities can be substituted for the Klenow enzymes. Example of such polymerases are the modified T7 DNA polymerase (Sequenase, USB Biochemicals (Cleveland, Ohio)), and the thermophilic Bst DNA polymerase large fragment (NEB). The final yield of amplified DNA may differ depending on the polymerase used and the length of incubation at 37° C. The concentration of DNMT-1 used in conjunction with each polymerase was determined experimentally by varying the amount of DNMT-1 added to each reaction.

The methylation pattern of the DNA can be investigated using methods known in the arts, such as methylation-sensitive restriction enzyme digests, methylation-specific PCR (MS-PCR), or real-time PCR. An example of MS-PCR is described below.

Example 2

This example demonstrates how a transposon can be inserted into the genomic DNA prior to methylation-coupled, whole genomic amplification.

The transposition reaction was performed using a commercially available kit from Epicentre (cat. # TSM99K2) designed to insert a transposon carrying the kanamycin resistance gene into the target DNA. Primers designed to anneal to the transposon DNA were used to initiate the methylation-coupled amplification reaction.

One µg of tumor DNA was incubated in 10 µl of transposase buffer (1× transposase buffer: 50 mM Tris-acetate, pH 7.5, 150 mM potassium acetate, 10 mM magnesium acetate, 4 mM spermidine) containing 1 unit of transposase and 0.081 µg of transposable DNA. The reaction was incubated at 37° C. for 2 hrs. The reaction was placed on ice, and 1 µl of 100 mM EDTA, pH 8.0, and 90 µl of TE8 were added to dilute the DNA to 10 ng/µl. The amount of transposon can be modified to change the average number of insertion events per kb of genomic DNA.

The methylation-coupled amplification was performed as described in Example 1, except that the following primers were used instead of the random GGGN6: Kan2-F1 (caaagctctcatcaacc; SEQ ID NO: 14) and Kan2-R1 (gcaatgtaacatcagaga; SEQ ID NO: 15), Kan2-F2 (actgtctgcttacataaa; SEQ ID NO: 16) and Kan2-R2 (aggtggaccagttgg; SEQ ID NO: 17). Other primers, which can anneal to both strands of the transposon also can be used.

Example 3

This example demonstrates methylation-coupled amplification of concatenated DNA.

Fragmented DNA was isolated from a cell line treated to induce apoptosis.

The Cell line CCL119 was obtained from the American Type Culture Collection (ATCC, Manassas, Va.) and propagated in modified RPMI 1640 medium supplemented with 10% fetal bovine serum (ATCC) according to the conditions provided by the supplier. To induce apoptosis, cycloheximide (Sigma, Saint Louis, Mo.) was added to the media to a final concentration of 200 µM, and the cells were incubated at 37° C. for an additional 72 hrs before harvesting. The DNA was purified using proteinase K digest, phenol/chloroform extraction, and ethanol precipitation, and resuspended in TE8 (Methods in Enzymology, supra). To recover degraded fragments, 20 µg of DNA were separated on a preparative 1.2% agarose gel. DNA fragments between 150 and 500 bp were recovered using the QIAEX II gel extraction kit from Qiagen. The recovery of the DNA was verified by running a small aliquot on a 7.5% acrylamide gel.

The DNA termini were repaired to generate blunt-ends suitable for ligation using the End-It Repair kit (Epicentre), which contains a combination of a DNA polymerase with proof-reading capabilities and a T4 polynucleotide kinase. The DNA was incubated for 45 min at RT in 20 µl of 1× buffer (33 mM Tris-acetate, pH 7.8, 66 mM potassium acetate, 10 mM magnesium acetate, and 0.5 mM DTT) containing 1 mM ATP, 0.25 mM dNTP mix, and 0.5 µl of the enzyme mix. The reaction was terminated by incubation at 70° C. for 15 min. DNA ligase was added to a concentration of 0.1 Unit/µl (Epicentre) without further manipulation, and the reaction was incubated at RT for 16 hours. The DNA was used directly without further purification. The DNA templates generated following the ligation reaction served as templates for the amplification procedures as follows. 10 ng of ligated DNA and 100 ng of GGGN6 in 5 ml of TE8 were denatured by adding an equal volume of freshly prepared 50 mM KOH and incubating at RT for 5 min. The reaction was neutralized by adding 5 µl of a freshly prepared solution of 50 mM Tris, pH 7.9, and 50 mM HCl.

The amplification reaction was set up in a final volume of 50 µl, by adding the following reagents to give the final concentrations indicated below:

1× NEB ThermoPol Buffer (20 mM Tris-HCl, 10 mM $(NH_4)_2SO_4$, 10 mM KCl, 2 mM $MgSO_4$, 0.1% Triton X-100, pH 8.3), 500 µM dATP, dCTP, dGTP, and dTTP, and 160 µM S-adenosylmethionine, and 10 ng/µl of BSA. The reaction was equilibrated at 37° C. for 5 min, followed by the addition of DNMT-1 (0.3 units/µl), and BST DNA polymerase (used at 37° C.), large fragment, to a final concentration of 0.167 units/µl.

The reaction was incubated at 37° C. for 6 min, and was stopped by the addition of EDTA to a final concentration of 50 mM. A 5 µl aliquot was separated on a 0.8% agarose gel as described above. The amplified DNA was used directly for sodium bisulfite treatment without further manipulation.

Example 4

This example demonstrates bisulfite treatment and detection of methylation using methylation-specific PCR.

The bisulfite treatment was performed in accordance with a modification of the methods of Frommer et al. (PNAS USA 89: 1827-1831 (1992)) as described below. DNA from a human lymphoblastoid cell line was treated with SssI methylase (NEB) according to supplier's conditions to generate fully methylated DNA as a positive control.

One μg of amplified DNA in 50 μl of TE8 was denatured by incubation in a final concentration of 0.2 M NaOH at 40° C. for 10 min. 600 μl of a freshly prepared 44% sodium bisulfite solution (pH 5.2 with 10 N NaOH) and 3 μl of 400 mM hydroquinone were added to the denatured DNA. The solution was incubated in a PCR machine for 8 cycles of 94° C. for 5 min, 55° C. for 120 min.

Following bisulfite treatment, the DNA was purified using a glass milk purification procedure according to the manufacturer's protocol (QIAEX II, Qiagen). The DNA was eluted in 100 μl of TE8. One-tenth volume of 3M NaOH was added, and the DNA was incubated at room temperature for 15 min. The DNA was precipitated by the addition of 0.66 volume of 5 M ammonium acetate, 1 μg of linear acrylamide (carrier), and 3 volumes of ethanol.

The DNA was resuspended in 20 μl of TE8, and stored frozen at −20° C. until PCR amplification. One to 4 μl of DNA was used for each PCR reaction. All PCR reactions were performed for 40 cycles of 95° C. for 15 sec, 62° C. for 20 sec, and 72° C. for 20 sec, except that the annealing temperature for the GSTP1 primer sets 1 and 2 was 65° C. Each reaction was carried out in a 30 μl final volume of 1× Eppendorf PCR buffer, 0.25 mM dNTPS, 12.5 pmoles of each primer, and 0.5 units of Taq enzyme (Eppendorf). The following table shows a list of primers used for the amplification reactions.

| Name | Size in bp |
|---|---|
| NRG1-Set1 | 119 |
| Forward Primer: GAGCGGGTAGCGAGAGTTTCGG; SEQ ID NO: 18 | |
| Reverse Primer: TAACGACGCGACTACCGAAAACC; SEQ ID NO: 19 | |
| GSTP1-Set1 | 132 |
| Forward Primer: CGGCGATTTCGGGGATTTTAGGGC; SEQ ID NO: 20 | |
| Reverse Primer: CCCCAATACTAAATCACGACGCCG; SEQ ID NO: 21 | |
| GSTP2-Set2 | 70 |
| Forward Primer: ACGTTCGGGGTGTAGCGGTCGTC; SEQ ID NO: 22 | |
| Reverse Primer: GACCGCTCTTCTAAAAAATCCCGCG; SEQ ID NO: 23 | |
| GSTP1-Set3 | 99 |
| Forward Primer: GGTCGGCGTCGTGATTTAGTATTGG; SEQ ID NO: 24 | |
| Reverse Primer: ACTACGACGACGAAACTCCAACGA; SEQ ID NO: 25 | |

The products of the amplification reactions were separated on an 8% acrylamide gel. The amplification product was detectable when the CpG island was methylated in the input DNA. The GSTP1 primers were used for the amplification of the prostate cancer DNA. The NRG-1 primers were used for the amplification of the CCL119 DNA. The SssI treated DNA was the positive control and showed an amplification product of the correct size for all 4 assays. The DNA amplified without DNMT-1 was the negative control and failed to show amplification for all 4 assays. The prostate tumor DNA showed an amplification product of the correct size for all three GSTP1 assays. The CCL119 showed an amplification product of the correct size for the NRG1 assay.

All references, including publications, patent applications, and patents, cited herein are hereby incorporated by reference to the same extent as if each reference were individually and specifically indicated to be incorporated by reference and were set forth in its entirety herein.

The use of the terms "a," "an," "the," and similar referents in the context of describing the invention (especially in the context of the following claims) is to be construed to cover the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended to illustrate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. A method for copying the methylation patterns of molecules of genomic DNA (MGD) during isothermal amplification of the MGD, which method comprises:
   (i) obtaining MGD,
   (ii) copying the methylation patterns of the MGD using a DNA methylation-maintenance enzyme, while isothermally amplifying the MGD using a DNA polymerase with strand displacement activity, under conditions that simultaneously promote activity of the DNA methylation-maintenance enzyme and the DNA polymerase with strand displacement activity, wherein the DNA methylation-maintenance enzyme is DNA methyltransferase 1 (DNMT-1) and wherein the DNMT-1 is optionally modified to reduce or eliminate de novo methylation activity, and
   (iii) optionally purifying the MGD, whereupon the MGD are amplified and their methylation patterns are copied.

2. The method of claim 1, wherein the DNMT-1 is from a eukaryote.

3. The method of claim 2, wherein the eukaryote is a human.

4. The method of claim 1, wherein the MGD are completely or partially double-stranded, and wherein the method further comprises contacting the MGD with transposable elements and an enzyme to randomly insert the transposable elements into the MGD to provide MGD comprising the randomly inserted transposable elements.

5. The method of claim 1, wherein the conditions that simultaneously promote activity of the DNA methylation-maintenance enzyme and the DNA polymerase with strand displacement activity comprise the presence of a buffer comprising a divalent ion, deoxynucleotide triphosphates (dNTPs), primers, and S-adenosyl-methionine (SAM).

6. The method of claim 1, wherein step (ii) further comprises:
   (i') mixing the MGD and primers, wherein either of (a) the MGD or (b) the MGD and the primers are optionally denatured before or after mixing,
   (ii') incubating the mixture of (i') at a temperature from about 0° C. to about 75° C. for a sufficient amount of time to allow annealing of the primers to the MGD,
   (iii') equilibrating the mixture of (ii') to a temperature for methyltransferase activity,
   (iv') adding a buffer, which comprises a divalent ion, dNTPs, primers, and SAM, and which is already equilibrated to the temperature of (iii'), and simultaneously with or sequentially to adding the buffer, adding the DNA methylation-maintenance enzyme and the DNA polymerase with strand displacement activity to the mixture of (iii'), and
   (v') incubating the mixture of (iv') at a temperature for methyltransferase activity to allow methylation-coupled amplification of the MGD until a desired amount is obtained of the MGD.

7. The method of claim 1, wherein the MGD are obtained from circulating DNA.

8. The method of claim 1, wherein the MGD comprise a mixture of fragments of strands of different length.

9. The method of claim 8, which further comprises contacting the MGD with an enzyme to provide MGD fragments with blunt ends.

10. The method of claim 9, wherein the blunt ends are generated by extending shorter strands of the fragments, by shortening longer strands of the fragments, or a combination thereof, optionally in the presence of a polynucleotide kinase.

11. The method of claim 9, which method further comprises contacting the MGD with an enzyme that ligates double-stranded nucleic acids under reaction conditions that promote ligation, optionally in the presence of a polynucleotide kinase.

12. The method of claim 10, which method further comprises contacting the MGD with an enzyme that ligates double-stranded nucleic acids under reaction conditions that promote ligation, optionally in the presence of a polynucleotide kinase.

13. A composition for methylation-coupled amplification of DNA comprising a DNMT-1, a DNA polymerase with strand displacement activity, and a buffer comprising a divalent ion, dNTPs, primers, and SAM, wherein the buffer is suitable for simultaneously promoting the activity of a DNA methylation-maintenance enzyme and a DNA polymerase with strand displacement activity and wherein the composition lacks a divalent cation chelator.

* * * * *

SEQUENCE LISTING

<160> NUMBER OF SEQ ID NOS: 25

<210> SEQ ID NO 1
<211> LENGTH: 24
<212> TYPE: DNA
<213> ORGANISM: Artificial
<220> FEATURE:
<223> OTHER INFORMATION: Synthetic primer
<220> FEATURE:

```
<221> NAME/KEY: misc_feature
<222> LOCATION: (9)..(9)
<223> OTHER INFORMATION: "n" may be any nucleotide

<400> SEQUENCE: 1
ttcarcacny tsathccamt ggtg                                              24

<210> SEQ ID NO 2
<211> LENGTH: 20
<212> TYPE: DNA
<213> ORGANISM: Artificial
<220> FEATURE:
<223> OTHER INFORMATION: Synthetic primer

<400> SEQUENCE: 2
athccmtggt gyctdcchca                                                   20

<210> SEQ ID NO 3
<211> LENGTH: 23
<212> TYPE: DNA
<213> ORGANISM: Artificial
<220> FEATURE:
<223> OTHER INFORMATION: Synthetic primer

<400> SEQUENCE: 3
aachgvcaya aymactgggc bgg                                               23

<210> SEQ ID NO 4
<211> LENGTH: 23
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: "n" may be any nucleotide
<220> FEATURE:
<221> NAME/KEY: misc_feature
<222> LOCATION: (18)..(18)
<223> OTHER INFORMATION: "n" may be any nucleotide
<220> FEATURE:
<221> NAME/KEY: misc_feature
<222> LOCATION: (21)..(21)
<223> OTHER INFORMATION: "n" may be any nucleotide

<400> SEQUENCE: 4
gantgyttyc aycargcngg nat                                               23

<210> SEQ ID NO 5
<211> LENGTH: 23
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: "n" may be any nucleotide
<220> FEATURE:
<221> NAME/KEY: misc_feature
<222> LOCATION: (15)..(15)
<223> OTHER INFORMATION: "n" may be any nucleotide
<220> FEATURE:
<221> NAME/KEY: misc_feature
<222> LOCATION: (18)..(18)
<223> OTHER INFORMATION: "n" may be any nucleotide

<400> SEQUENCE: 5
atgggntayc artcnacntt ygg                                               23
```

<210> SEQ ID NO 6
<211> LENGTH: 24
<212> TYPE: DNA
<213> ORGANISM: Artificial
<220> FEATURE:
<223> OTHER INFORMATION: Synthetic primer

<400> SEQUENCE: 6
tayctsagct actgtgacta ytac                                              24

<210> SEQ ID NO 7
<211> LENGTH: 25
<212> TYPE: DNA
<213> ORGANISM: Artificial
<220> FEATURE:
<223> OTHER INFORMATION: Synthetic primer

<400> SEQUENCE: 7
tggaraatgt ccgkaacttt gtatc                                             25

<210> SEQ ID NO 8
<211> LENGTH: 25
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (9)..(9)
<223> OTHER INFORMATION: "n" may be any nucleotide
<220> FEATURE:
<221> NAME/KEY: misc_feature
<222> LOCATION: (15)..(15)
<223> OTHER INFORMATION: "n" may be any nucleotide

<400> SEQUENCE: 8
aabccytgng abcgngcrca ytccc                                             25

<210> SEQ ID NO 9
<211> LENGTH: 23
<212> TYPE: DNA
<213> ORGANISM: Artificial
<220> FEATURE:
<223> OTHER INFORMATION: Synthetic primer

<400> SEQUENCE: 9
tgggacgght tcttcagyac hac                                               23

<210> SEQ ID NO 10
<211> LENGTH: 23
<212> TYPE: DNA
<213> ORGANISM: Artificial
<220> FEATURE:
<223> OTHER INFORMATION: Synthetic primer

<400> SEQUENCE: 10
gcrcactccc tsacrctcac cac                                               23

<210> SEQ ID NO 11
<211> LENGTH: 23
<212> TYPE: DNA
<213> ORGANISM: Artificial
<220> FEATURE:
<223> OTHER INFORMATION: Synthetic primer

<400> SEQUENCE: 11
gtdgtrctga agaadccgtc cca          23

<210> SEQ ID NO 12
<211> LENGTH: 16
<212> TYPE: DNA
<213> ORGANISM: Artificial
<220> FEATURE:
<223> OTHER INFORMATION: Synthetic primer

<400> SEQUENCE: 12
cactgcactc cagcct          16

<210> SEQ ID NO 13
<211> LENGTH: 15
<212> TYPE: DNA
<213> ORGANISM: Artificial
<220> FEATURE:
<223> OTHER INFORMATION: Synthetic primer

<400> SEQUENCE: 13
ggtctcgatc tcctg          15

<210> SEQ ID NO 14
<211> LENGTH: 17
<212> TYPE: DNA
<213> ORGANISM: Artificial
<220> FEATURE:
<223> OTHER INFORMATION: Synthetic primer

<400> SEQUENCE: 14
caaagctctc atcaacc          17

<210> SEQ ID NO 15
<211> LENGTH: 18
<212> TYPE: DNA
<213> ORGANISM: Artificial
<220> FEATURE:
<223> OTHER INFORMATION: Synthetic primer

<400> SEQUENCE: 15
gcaatgtaac atcagaga          18

<210> SEQ ID NO 16
<211> LENGTH: 18
<212> TYPE: DNA
<213> ORGANISM: Artificial
<220> FEATURE:
<223> OTHER INFORMATION: Synthetic primer

<400> SEQUENCE: 16
actgtctgct tacataaa          18

<210> SEQ ID NO 17
<211> LENGTH: 15
<212> TYPE: DNA
<213> ORGANISM: Artificial
<220> FEATURE:
<223> OTHER INFORMATION: Synthetic primer

<400> SEQUENCE: 17
aggtggacca gttgg          15

<210> SEQ ID NO 18
<211> LENGTH: 22
<212> TYPE: DNA
<213> ORGANISM: Artificial

```
<220> FEATURE:
<223> OTHER INFORMATION: Synthetic primer

<400> SEQUENCE: 18
gagcgggtag cgagagtttc gg                                              22

<210> SEQ ID NO 19
<211> LENGTH: 23
<212> TYPE: DNA
<213> ORGANISM: Artificial
<220> FEATURE:
<223> OTHER INFORMATION: Synthetic primer

<400> SEQUENCE: 19
taacgacgcg actaccgaaa acc                                             23

<210> SEQ ID NO 20
<211> LENGTH: 24
<212> TYPE: DNA
<213> ORGANISM: Artificial
<220> FEATURE:
<223> OTHER INFORMATION: Synthetic primer

<400> SEQUENCE: 20
cggcgatttc ggggatttta gggc                                            24

<210> SEQ ID NO 21
<211> LENGTH: 24
<212> TYPE: DNA
<213> ORGANISM: Artificial
<220> FEATURE:
<223> OTHER INFORMATION: Synthetic primer

<400> SEQUENCE: 21
ccccaatact aaatcacgac gccg                                            24

<210> SEQ ID NO 22
<211> LENGTH: 23
<212> TYPE: DNA
<213> ORGANISM: Artificial
<220> FEATURE:
<223> OTHER INFORMATION: Synthetic primer

<400> SEQUENCE: 22
acgttcgggg tgtagcggtc gtc                                             23

<210> SEQ ID NO 23
<211> LENGTH: 25
<212> TYPE: DNA
<213> ORGANISM: Artificial
<220> FEATURE:
<223> OTHER INFORMATION: Synthetic primer

<400> SEQUENCE: 23
gaccgctctt ctaaaaaatc ccgcg                                           25

<210> SEQ ID NO 24
<211> LENGTH: 25
<212> TYPE: DNA
<213> ORGANISM: Artificial
<220> FEATURE:
<223> OTHER INFORMATION: Synthetic primer

<400> SEQUENCE: 24
ggtcggcgtc gtgatttagt attgg                                           25
```

```
<210> SEQ ID NO 25
<211> LENGTH: 24
<212> TYPE: DNA
<213> ORGANISM: Artificial
<220> FEATURE:
<223> OTHER INFORMATION: Synthetic primer

<400> SEQUENCE: 25
actacgacga cgaaactcca acga                                           24
```